(12) United States Patent
Sanada

(10) Patent No.: US 7,319,168 B2
(45) Date of Patent: Jan. 15, 2008

(54) PROCESS FOR PRODUCING ALIPHATIC CARBOXYLIC ACID

(75) Inventor: Kenji Sanada, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 427 days.

(21) Appl. No.: 10/844,314

(22) Filed: May 13, 2004

(65) Prior Publication Data
US 2004/0254398 A1    Dec. 16, 2004

(30) Foreign Application Priority Data
May 13, 2003    (JP)    ............... 2003-134887

(51) Int. Cl.
*C07C 51/42*    (2006.01)
(52) U.S. Cl. ..................................... 562/600
(58) Field of Classification Search ............... 562/598, 562/600, 523
See application file for complete search history.

(56) References Cited

U.S. PATENT DOCUMENTS 5,910,607 A * 6/1999 Sakakura et al. ........... 562/532
6,448,438 B1    9/2002 Yada et al.

FOREIGN PATENT DOCUMENTS

| GB | 2 146 636 A | 4/1985 |
|---|---|---|
| JP | 6-15495 | 2/1985 |
| JP | 10-298133 | 11/1998 |
| JP | 2000-281617 A | 10/2000 |
| JP | 2002-1005 A | 1/2002 |
| WO | 199845239 | * 10/1998 |
| WO | 200197941 | * 12/2001 |
| WO | WO-01/97941 A1 | 12/2001 |

* cited by examiner

*Primary Examiner*—Karl Puttlitz
(74) *Attorney, Agent, or Firm*—Connolly Bove Lodge and Hutz

(57) ABSTRACT

It is an object of the present invention to provide a process for producing aliphatic carboxylic acid, which can stabilize operation of a distillation column upon production of aliphatic carboxylic acid by reducing a water content in an aqueous aliphatic carboxylic acid solution by a distillation column, and can shorten a time during the non-steady state such as at starting up of distillation column operation. The present invention is directed to a process for producing aliphatic carboxylic acid, which comprises an azeotropic distillation step of supplying an aqueous aliphatic carboxylic acid solution and an azeotropic solvent to an azeotropic distillation column to perform distillation, separating an azeotrope containing the azeotropic solvent and water as a distillate, and recovering aliphatic carboxylic acid with a reduced water content as bottom liquid, characterized in that a target value of an amount of the azeotropic solvent to be supplied is set depending on an amount of water in the aqueous aliphatic carboxylic acid solution supplied to the azeotropic distillation column, and the amount of the azeotropic solvent to be supplied is controlled at the target value.

8 Claims, 1 Drawing Sheet

PROCESS FOR PRODUCING ALIPHATIC CARBOXYLIC ACID

TECHNICAL FIELD

The present invention relates to a process for producing aliphatic carboxylic acid. More particularly, the present invent ion relates to a process for producing aliphatic carboxylic acid useful in various utilities, by distilling an aqueous aliphatic carboxylic acid to reduce a water content and the like.

BACKGROUND ART

Aliphatic carboxylic acid is industrially useful as a raw material for preparing various compounds and polymers and, among them, an easily polymerizable substance having the polymerizability which easily causes a polymerization reaction by the heat or the like, such as (meth) acrylic acid and the like, is industrially particularly useful.

For example, (meth) acrylic acid is widely used for forming an acrylic fiber copolymer, and an adhesive such as emulsion and the like, additionally, is useful also in the fields such as paint, fabric processing, leather, construction material and the like, and is becoming indispensable in many chemical fields.

As a process for producing such the aliphatic carboxylic acid, for example, in preparation of (meth)acrylic acid, a process by a catalytic gas phase oxidation reaction of propylene or the like has advantage that an inexpensive raw material can be used, being industrially advantageous. In this case, (meth) acrylic acid is produced by absorbing a product in water and, thereafter, performing distillation procedure with an azeotropic solvent to separate from water. In such the step, side products such as a low boiling point substance, a high boiling point substance and the like which are produced as a by-product in addition to (meth) acrylic acid, as well as other impurities are separated and removed by purification system composed of a distillation column and the like, and purified high quality (meth) acrylic acid is supplied. Like this, a process using a distillation column allows a water content in an aqueous solution of aliphatic carboxylic acid such as (meth) acrylic acid and the like to be reduced, thus, aliphatic carboxylic acid useful in various utilities can be produced. However, in a distillation column used in such process, it is difficult to stabilize operation, and the distillation column is in the non-steady state during starting up. For example, when (meth) acrylic acid is purified, since a change in a temperature distribution in the distillation column and a change in the concentration of bottom liquid are easily caused due to a variation of a process resulting from a variation in an aqueous aliphatic carboxylic acid solution supplied to a distillation column, there is demanded a method which can stabilize operation of a distillation column.

As the previous process using a distillation column, for example, there can be exemplified the following method.

With respect to an azeotropic distillation method, there is disclosed a method of controlling a distillation column by an amount of entrainer to be supplied, an refluxing amount and a heating amount by setting an amount of an entrainer to be retained in the distillation column in Japanese Kokai Publication 2002-1005 (p.1). However, since a target value of an amount of an entrainer to be retained is set by a change in a temperature in a column or a composition of bottom liquid, there is a time lag from confirmation of a variation f a process to a change in an amount of an entrainer to be supplied, a refluxinq amount and a heating amount in response to the variation and, therefore, there is room for a contrivance to effectively control a variation of a process.

With respect to a process for producing acrylic acid, there is disclosed a method of supplying an azeotropic solvent so that a column top vapor composition at a distillation column becomes an azeotropic composition at an operation pressure, and obtaining a mixture containing mainly acrylic acid and acetic acid which does not contain water and an azeotropic solvent, from a column bottom in Japanese Kokoku Publication Hei-06-15495 (P.1-2). However, since there is no description of control in response to a variation of a process, there is room for study.

With respect to a method of purifying acrylic acid, there is disclosed that the higher concentration of an azeotropic solvent in bottom liquid in a dehydration distillation column is better, and that a temperature at a part corresponding to the 2nd plate of theoretical plate which is counted from a bottom is 60 to 73° C. in Japanese Kokai Publication 2000-281617 (p.2-3). In addition, in Example, there is described that the composition of bottom liquid is 2.3% of acetic acid, 0.6% of water and 15% of toluene. However, since this method is temperature control, and there is a time lag, there is room for a contrivance to overcome a time lag also in such the method of purifying acrylic acid.

With respect to a method of recovering acetic acid, there is described a method of controlling a reflux ratio or a heating stream depending on an electric conductivity of a distillation column bottoms in Japanese Kokai Publication Hei-10-298133 (p. 2-3). However, since a change in a composition of a distillate or bottom liquid is detected, there is a time lag, and the effect is not expected in a variation of a process, there is a room for contrivance to stabilize operation of a distillation column and shorten a time during the non-steady state such as at starting up of distillation column operation, also in this method.

SUMMARY OF THE INVENTION

Accordingly, it is an object of the present invention, which has been made in view of the above-mentioned state of the art, to provide a process for producing aliphatic carboxylic acid, which can stabilize operation of a distillation column upon production of aliphatic carboxylic acid by reducing a water content in an aqueous aliphatic carboxylic acid solution by a distillation column, and can shorten a time during the non-steady state such as at starting up of distillation column operation.

The present inventors made various investigations concerning process for producing aliphatic carboxylic acid, paid their attention to that aliphatic carboxylic acid useful in various utilities can be produced by an azeotropic distillation step of supplying an aqueous aliphatic carboxylic acid solution and an azeotropic solvent to an azeotropic distillation column to perform distillation, separating an azeotrope as a distillate, and recovering aliphatic carboxylic acid with a reduced water content as bottom liquid, and found that the above object can be successfully attained by setting a target value of an amount of an azeotropic solvent to be supplied depending on an amount o f water in an aqueous aliphatic carboxylic acid solution supplied to an azeotropic distillation column, and controlling an amount of an azeotropic solvent to be supplied at the target value. These findings have now led to completion of the present invention. For example, when a heating amount is controlled by a temperature at a distillation column, or an amount of an azeotropic solvent supplied to an azeotropic distillation column is feed back-controlled, there is disadvantage that control is not stabilized due to a time lag. However, we found that, by changing an amount of an azeotropic solvent to be supplied is changed in advance according to the above-mentioned method, a variation in a temperature is decreased, and it becomes possible to improve the controllability.

That is, we found that, since the conditions for operating an azeotropic distillation column can be set at optimal before a change in a temperature and the separation state which were previously a subject to be controlled is caused, by detecting a change in an amount of aliphatic carboxylic acid to be supplied and the concentration of water in advance, operation of an azeotropic distillation column can be stabilized by overcoming a time lag in control of an azeotropic distillation column and, at the same time, a time during the non-steady state such as at starting up of azeotropic distillation column operation can be shortened.

In particular, when an apparatus is scaled up, since there is a tendency that a time lag to manifestation of influence on an azeotropic distillation column becomes great, this action and effect of the present invention are remarkably exerted.

In addition, when an easily polymerizable substance such as acrylic acid is handled, by stabilizing operation of an azeotropic distillation column or by shortening a time during the non-steady state at starting up, occurrence of polymerization trouble can be reduced.

That is, the present invention is a process for producing aliphatic carboxylic acid, which comprises an azeotropic distillation step of supplying an aqueous aliphatic carboxylic acid solution and an azeotropic solvent to an azeotropic distillation column to perform distillation, separating an azeotrope containing the azeotropic solvent and water as a distillate, and recovering aliphatic carboxylic acid with a reduced water content as bottom liquid, characterized in that a target value of an amount of the azeotropic solvent to be supplied is set depending on an amount of water in the aqueous aliphatic carboxylic acid solution supplied to the azeotropic distillation column, and the amount of the azeotropic solvent to be supplied is controlled at the target value.

Figure 1:
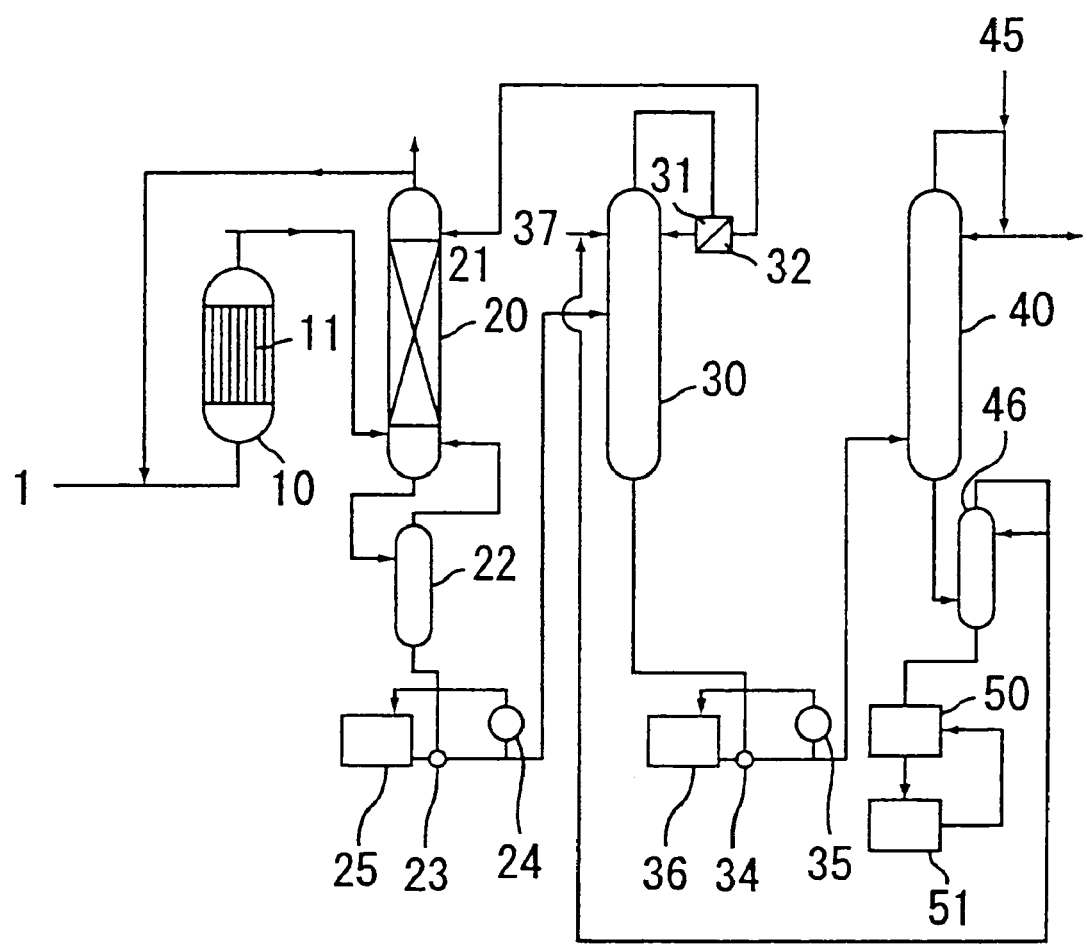
FIG. 1 is a flow figure showing outline of a step of producing acrylic acid including a step of supplying acrylic acid obtained in a reactor to a purifying apparatus.

EXPLANATION OF SYMBOLS 1. raw material gas
10. catalytic gas phase oxidation reactor (oxidation reactor)
11. catalyst for oxidation reaction
20. absorbing column
21. absorbing solvent
22. distillation column
23. pump
24. cooler
25. tank (intermediate tank)
30. azeotropic distillation column
31. solvent phase in oil and water separator
32. aqueous phase in oil and water separator
34. pump
35. cooler
36. tank
37. polymerization inhibitor
40. high boiling point substance separation column
45. polymerization inhibitor
46. maleic acid separation column
50. thin film evaporator
51. thermal decomposition vessel

DETAILED DESCRIPTION OF THE INVENTION

In the following, the present invention is described in detail.

In the process for producing aliphatic carboxylic acid of the present invention, at an azeotropic distillation step, an amount of an azeotropic solvent to be supplied corresponding to an amount of water supplied to an azeotropic distillation column is determined, and a target value of an amount of an azeotropic solvent is set. A method of determining an amount of an azeotropic solvent to be supplied is not particularly limited as long as it is a method of primarily determining an amount of an azeotropic solvent to be supplied in response to an amount of water to be supplied, but a method comprising setting a target value of the water concentration in a column top vapor (referred to as a target value 1) and calculating a target value of an azeotropic solvent to be supplied (referred to as a target value 2) in which the water concentration becomes said target value (target value 1) by calculating mass balance of an azeotropic distillation column, is preferable. It is preferable to set the target value of the water concentration in a column top vapor (target value 1) at a range of 10% by weight of the azeotropic composition of an azeotropic solvent and water at a column top pressure. In other words, the target value 1 is at a range of the azeotropic composition of an azeotropic solvent and water at a column top pressure ±10% by weight. In calculation of mass balance of azeotropic distillation column, mass balance between an aqueous aliphatic carboxylic acid solution and an azeotropic solvent as incoming liquids to the azeotropic distillation column, and an azeotrope containing an azeotropic solvent and water at a top of an azeotropic distillation column and bottom liquid as outgoing liquids from the column is calculated. For example, in the case where water is separated from an aqueous aliphatic carboxylic acid solution in an azeotropic distillation column, and aliphatic carboxylic acid with a sufficiently reduced water content is recovered as bottom liquid, the target value of the water concentration (target value 1) of a composition of an azeotrope at a top of an azeotropic distillation column (column top vapor composition) is set so that an azeotropic solvent and water are not discharged from bottom liquid, a target value of an amount of an azeotropic solvent to be supplied to an azeotropic distillation column (target value 2) is set from mass balance in an azeotropic distillation column so that the water concentration become the target value (target value 1), an amount of an azeotropic solvent to be supplied is determined so as to be the target value (target value 2), and an azeotropic solvent is supplied to an azeotropic distillation column, thereby, an amount of an azeotropic solvent to be supplied is controlled.

In the present invention, an amount of water in an aqueous aliphatic carboxylic acid solution supplied to an azeotropic distillation column is detected and, depending on the water amount, an amount of an azeotropic solvent to be supplied is controlled by the target value (target value 2) set as described above. The aqueous aliphatic carboxylic acid solution and the azeotropic solvent may be supplied to the azeotropic distillation column in the pre-mixed state, or separately. It is preferable that an amount of water in the aqueous aliphatic carboxylic acid solution is detected after the amount of the aqueous aliphatic carboxylic solution supplied to an azeotropic distillation column is set. The amount of water in the aqueous aliphatic carboxylic acid solution supplied to the azeotropic distillation column is preferably not more than 40% by weight, more preferably not less than 10% by weight and not more than 35% by weight.

As a method of detecting the above-mentioned amount of water supplied to the azeotropic distillation column, an amount of a solution to be supplied is measured with various flow meters, and the concentration of water in a solution to be supplied can be measured with various on-line analyzers. In particular, in the case of lower aliphatic carboxylic acid, since an electric conductivity of a solution varies depending on the water concentration, the water concentration can be detected by measuring an electric conductivity. This case is preferable since an expensive analyzing apparatus is not necessary.

As a preferable mode of the present invention, there is a mode that an amount of heat to be added to the above-mentioned azeotropic distillation column is adjusted so that the water concentration in bottom liquid of the azeotropic distillation column becomes not more than 500 ppm, and the azeotropic solvent concentration becomes not more than 500 ppm. When the water concentration and the azeotropic solvent concentration in bottom liquid are not more than 500 ppm, this becomes advantageous in purification at a later step. More preferably, the water concentration and/or azeotropic solvent concentration are (is) not more than 200 ppm, still preferably not more than 100 ppm.

In the above-mentioned azeotropic distillation step, by addition of heat to an azeotropic distillation column, an aqueous aliphatic carboxylic acid solution to be supplied is distilled together with an azeotropic solvent, and it is preferable that a set value of the amount of heat to be added to the azeotropic distillation column is determined by a specified plate temperature in the azeotropic distillation column. That is, it is preferable to select any plate in an azeotropic distillation column, and determine a set value of the amount of heat based on a temperature of that plate. When an amount of heating is controlled so that a temperature of a specified plate in an azeotropic distillation column becomes a certain target value, the above-mentioned bottoms composition in which the water concentration and the azeotropic solvent concentration are a certain value or smaller can be easily attained.

As the specified plate any plate In an azeotropic distillation column may be selected, but it is preferable that a temperature of the specified plate is a temperature at a part corresponding to a 5th or larger plate of theoretical plate and 15th or smaller, more preferably 6th or larger and 10th or smaller, still more preferably 7th or larger and 9th or smaller which is counted from a column top. A total plate number of an azeotropic distillation column is preferably 30 or larger, more preferably 40 or larger and 60 or smaller.

It is desirable that adjustment of the amount heat is performed by adjusting an amount of a heating medium to be supplied as the reboiler equipped a distillation column. As the reboiler, a shell and tube heat exchanger, a plate type heat exchanger, a spiral type heat exchanger and the like can be used.

When aliphatic carboxylic acid is an easily polymerizable substance, a polymerization trouble may occur in which a polymerization reaction occurs at a production step. However, in the process of the present invention, occurrence of a polymerization trouble can be prevented, and the effect of the present invention can be more sufficiently exerted. The easily polymerizable substance refers to a substance having the polymerizability which easily causes a polymerization reaction by the heat or the light and the like. For example, a monomer having a radical polymerizable double bond is preferable. More preferable is acrylic acid which is an easily polymerizable substance having high necessity of stable maintenance of a production amount.

The above-mentioned azeotropic solvent used in the present invention is not particularly limited as long as it forms an azeotrope with water, but is preferably at least one solvent selected from the group consisting of an aliphatic hydrocarbon having 7 to 8 carbon atoms, an aromatic hydrocarbon having 7 to 8 carbon atoms and a halogenated hydrocarbon having 2 to 6 carbon atoms. Thereby, for example, it becomes possible to effectively separate water from an aqueous aliphatic carboxylic acid solution by an azeotropic distillation column, and recover aliphatic carboxylic acid with a reduced water content as bottom liquid.

An apparatus for producing aliphatic carboxylic acid which comprises an azeotropic distillation column used for the process for producing aliphatic carboxylic acid, can stabilize operation of an azeotropic distillation column upon production of aliphatic carboxylic acid by reducing a water content of an aqueous aliphatic carboxylic acid solution by the azeotropic distillation column and, at the same time, can shorten a time during the non-steady state such as at starting up of operation of an azeotropic distillation column, being useful. Such the apparatus for producing aliphatic carboxylic acid is also one of the present inventions. By using such the production apparatus with controlling an amount of an azeotropic solvent to be supplied to an azeotropic distillation column depending on an amount of water in an aqueous aliphatic carboxylic acid solution to be supplied to an azeotropic distillation column, it becomes possible to overcome a time lag which was caused by the previous method, and the effect of the present invention can be exerted.

The above-mentioned azeotropic distillation column in an apparatus for producing aliphatic carboxylic acid has a column diameter of preferably not less than 2.5 m, more preferably not less than 3.0 m.

The process for producing aliphatic carboxylic acid of the present invention will be explained below using drawings in the case when aliphatic carboxylic acid is acrylic acid.

In the process of the present invention, when acrylic acid is produced, it is preferable to produce it by a catalytic gas phase oxidation reaction of a raw material gas such as propylene and the like from a viewpoint that an inexpensive raw material can be used. In this case, it is preferable to use propylene, propane, acrolein or the like as a raw material gas. In addition to such the raw material substance, a gas including molecular oxygen and an inert gas can be used.

FIG. 1 conceptionally shows an industrial facility when acrylic acid is produced as described above in the process for producing aliphatic carboxylic acid of the present invention.

In FIG. 1, a raw material gas 1 is introduced into a catalytic gas phase oxidation reactor 10, and a gas containing acrylic acid is produced by the reactor 10. The thus produced gas is supplied to an absorbing column 20, and absorbed in water to obtain an aqueous acrylic acid solution (acrylic acid-containing aqueous solution).

The above-mentioned aqueous acrylic acid solution is supplied to a distillation column 22, if necessary. At this distillation column 22, unnecessary low boiling point substances are removed and thereafter a column bottom liquid of a distillation column 22 is transferred to a cooler 24 and a tank 25 with pump 23.

Then, the aqueous acrylic acid solution is supplied to an azeotropic distillation column 30 and, there upon, a target value of an amount of an azeotropic solvent to be supplied is set depending on an amount of water in an aqueous acrylic acid solution supplied to the azeotropic distillation column 30, and an azeotropic solvent is supplied to the azeotropic distillation column 30 by controlling an amount of the azeotropic solvent to be supplied at the target value. In addition, by determining a set value of an amount of heat to be added to the azeotropic distillation column 30 by a temperature at a specified plate in the azeotropic distillation column 30, it becomes easy to sufficiently reduce the water concentration and the azeotropic solvent concentration in a column bottom liquid in the azeotropic distillation column 30, for example, to not more than 500 ppm of water concentration, and to not more than 500 ppm of the azeotropic solvent concentration. A temperature of a specified plate is preferably not less than 40° C., more preferably not less than 50° C. and not more than 80° C., still more preferably not less than 55° C., and not more than 70° C. An amount of heat to be added to the azeotropic distillation column 30 can be usually adjusted by determining an amount of water steam to be placed into the azeotropic distillation column 30.

The above-mentioned aqueous acrylic acid solution to be supplied to the azeotropic distillation column 30 usually contains acetic acid and other impurities in addition to acrylic acid and water, and the acetic acid concentration at a column bottom of the distillation column 30 is preferably 0.02 to 2% by weight.

As the above-mentioned azeotropic distillation column 30, a plate column, a packed column, a wetted wall column, a spray column and the like can be used. As the azeotropic distillation column 30, the plate column or the packed column is usually preferable like the absorbing column 20. A column top pressure in the azeotropic distillation column 30 is preferably 20 to 200 hPa (abs.). A column top temperature is determined by an azeotropic composition determined depending on this column top pressure. (abs.) is an absolute pressure.

An oil and water separator is disposed in the azeotropic distillation column 30, a distillate from a column top part is introduced therein to separate into a solvent phase 31 in the oil and water separator and an aqueous phase 32 in the oil and water separator, the oil phase 31 is refluxed to the azeotropic distillation column 30 at a reflux ratio of 0.5 to 10, and the aqueous phase 32 is circulated into an absorbing column 20, which is preferably used as an absorbing solvent 21.

Then, a column bottom liquid of the azeotropic distillation column 30 is transferred to a cooler 35 and a tank 36 with a pump 34, and is supplied to a high boiling point substance separation column 40 which is a purification apparatus. Acrylic acid which has been purified there is obtained as distillate.

The above-mentioned column bottom liquid of the high boiling point substance separation column 40 containing an acrylic acid oligomer and maleic acid is supplied to a column bottom of a maleic acid separation column 46. A part of acrylic acid obtained as a distillate of the maleic acid separation column 46 is supplied to the azeotropic distillation column 30 and, at the same time, an acrylic acid oligomer-containing solution is concentrated in a thin film evaporator 50, and thermally decomposed in a thermal decomposition vessel 51 to obtain purified acrylic acid. From a viewpoint of improvement in a yield of acrylic acid, it is preferable to supply a part of a distillate of the maleic acid separation column 46 to the azeotropic distillation column 30. In addition, it is preferable to supply a polymerization inhibitor to the high boiling point substance separation column 40, thereby, a polymerization reaction can be prevented to improve a yield of acrylic acid.

In the above-mentioned process, it is preferable to use a multitubular reactor as the reactor 10 in that it is excellent in a reaction efficiency. For example when acrolein is used as a raw material substance, acrylic acid can be produced by a one-stage catalytic gas phase oxidation reaction and, when propylene is used as a raw material substance, acrylic acid can be produced by a two-stage catalytic gas phase oxidation reaction.

In the above two-stage catalytic gas phase oxidation reaction, since a reaction rate can be enhanced, it is preferable to perform the reaction in the presence of a catalyst, and a catalyst can be used at a former stage and a latter stage. As the former stage catalyst, for example, a compound represented by the following general formula (1) is preferable.

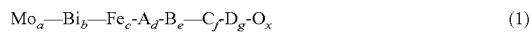

$$Mo_a\text{—}Bi_b\text{—}Fe_c\text{-}A_d\text{-}B_e\text{—}C_f\text{-}D_g\text{-}O_x \qquad (1)$$

In the above general formula (1), Mo, Bi and Fe denote molybdenum, bismuth and iron, respectively. A denotes at least one element selected from nickle (Ni) and cobalt (Co). B denotes at least one element selected from an alkali metal and thallium (Tl). C denotes at least one element selected from the group consisting of phosphorus (P), niobium (Nb), manganese (Mn), cerium (Ce), tellurium (Te), tungsten (W), antimony (Sb) and lead (Pb). D denotes at least one element selected from the group consisting of silicon (Si), alminum (Al), zirconium (Zr), and titanium (Ti). O denotes an oxygen atom. Symbols a, b, c, d, e, f, g and x denote an atomic ratio of Mo, Bi. Fe, A, B, C, D and O, respectively. And, when a=12, then b=0.1 to 10, c=0.1 to 10, d=2 to 20, e=0.001 to 5, f=0 to 5, g=0 to 30 and x is a value determined by the oxidation state of each element.

As the above-mentioned latter stage catalyst, a compound represented by the following general formula (2) and the like is preferable.

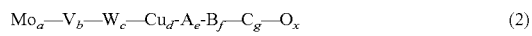

$$Mo_a\text{—}V_b\text{—}W_c\text{—}Cu_d\text{-}A_e\text{-}B_f\text{—}C_g\text{—}O_x \qquad (2)$$

In the above general formula (2), Mo, V, W and Cu denote molybdenum, vanadium tungsten and copper, respectively. A denotes at least one element selected from antimony, bismuth, tin, niobium, cobalt, iron, nickle and chromium (Cr). B denotes at least one element selected from an alkali metal, an alkaline earth metal and thallium. C denotes at least one element selected from silicon, alminuml zirconium and cerium. O denotes an oxygen atom. Symbols a, b, c, d, e, f, g and x denote an atomic ratio of Mo, V, W, Cu, A, B. C and O. And, when a=12, then b=2 to 14, c=0 to 12, d=0.1 to 5, e=0 to 5, f=0 to 5, g=0 to 20, and x is a value determined by the oxidation state of each element.

In the above FIG. 1 acrylic acid is obtained in the gas aqueous state by a catalytic gas phase oxidation reaction, and the acrylic acid-containing gas is supplied to an absorbing column 20. In this case, as an absorbing method, it is preferable to supply a solvent 21 to the absorbing column 20 and absorb it with the solvent. As the solvent, it is preferable to use an aqueous solvent having advantages that it is inexpensive and waste water discharged from such the production step can be reused.

When the acrylic acid-containing gas contains unreacted raw material substances, the raw material substances are removed by distillation or stripping and, thereafter, the gas may be supplied to the absorbing column 2. In addition, it is preferable to supply the acrylic acid-containing gas to the absorbing column 20 after cooling since an absorbing efficiency is improved.

As the absorbing column 20, an absorbing column such as a plate column, a packed column and the like can be used and, usually, it is preferable to use the plate column or the packed column.

A column top pressure in the absorbing column 20 is not limited as long as it is a pressure at which a gas can be discharged from a column top, but the pressure is preferably 0 to 30 kPa (gauge pressure). When the pressure is lower than 0 kPa (gauge pressure), an evacuating apparatus becomes necessary and, when the pressure is higher than 30 kPa (gauge pressure), it becomes necessary to up a blower capacity for supplying a raw material gas to a catalytic gas phase oxidation reactor. A dilution gas and unreacted raw material components among a gas discharged from a column top can be utilized again in a reaction by circulating them into a reactor 10 in FIG. 1.

An aqueous acrylic acid solution of the absorbing column 20 may be supplied to a distillation column 22, if necessary, to remove unnecessary low boiling point substances.

In the above azeotropic distillation column 30, it is preferable to appropriately add a polymerization inhibitor in order to prevent polymerization of acrylic acid. By azeotropic dehydration treatment in the above azeotropic distillation column 30, water and low boiling point substances contained in an aqueous acrylic acid solution are removed, and a water separation step and a low boiling point substance separation step may be performed separately. In general, after dehydration treatment, acrylic acid can be further purified by a high boiling point substance separation step, or other previously known purification method alone or in combination thereof. A method of purification is not limited to a distillation method, but acrylic acid :nay be purified by crystallization.

Bottom liquid from the above azeotropic dehydration step and/or low boiling point substances separation step are supplied to a highly boiling point substance separation column 40.

As the above high boiling point substance separation column 40, a plate column, a packed column, a wetted wall column, a spray column and the like can be used.

As the distillation conditions in the above high boiling point substance separation column 40, the previously known distillation conditions can be used. For example, distillation can be performed at a column top pressure of 20 to 200 hPa (abs.) and a column bottom temperature of not more than 120° C.

A column bottom liquid in the above high boiling point substance separation column 40 contains a polymerization inhibitor, an acrylic acid oligomer, and other high boiling point substances. It is preferable to perform a step of thermally decomposing an acrylic acid oligomer contained in this column bottom liquid, and recovering acrylic acid.

Thermal decomposition of the acrylic acid oligomer is performed in a thermal decomposition vessel 51. A form of the thermal decomposition vessel 51 is not particularly limited, but since a column bottom liquid supplied from a high boiling point substance separation column 40 has a high viscosity and, occasionally, bad fluidity because of a deposit, it is preferable that there is a inclination toward a liquid ejection exit and a solution circulating and/or stirring machine is (are) disposed so that a composition in a tank can be uniformized.

In order to obtain the above-mentioned decomposed solution, it is preferable to dispose a distillation facility such as a maleic acid separation column 46 and the like at an upper part of the decomposition vessel 51. A column bottom liquid supplied from the high boiling point substance separation column 40 is supplied to a maleic acid separation column 46, a column bottom liquid obtained from the maleic acid separation column 46 is concentrated in a thin film evaporator 50, and supplied to the thermal decomposition vessel 51 to decompose an oligomer. As the thin film evaporator 50, any form of a horizontal type and a vertical type can be used in that even a high viscosity solution can be concentrated. In the process of FIG. 1, a solution obtained from the thermal decomposition vessel 51 is concentrated again in the thin film evaporator 50, and acrylic acid obtained by thermal decomposition is recovered. In the thin film evaporator 50, since acrylic acid is evaporated, the acrylic acid may be recovered from a column top part of the maleic acid separation column 46.

As conditions at distillation in the maleic acid separation column 46, a number of theoretical plate is preferably 1 to 10, more preferably 1 to 5, and it is preferable that distillation is performed at a column top pressure of 10 to 150 hPa (abs.) and at a column bottom temperature of not more than 120° C.

In addition, in thermal decomposition in the maleic acid separation column 46, the thin film evaporator 50 or the thermal decomposition vessel 51, a polymerization inhibitor may be added. In some cases, polymerization can be effectively prevented and thermal decomposition is promoted.

It is p referable that the above acrylic acid recovered by thermal decomposition of the oligomer is supplied to a dehydration step. As described above, thereby, impurities such as water and the like contained in the next step or later can be purified, and a polymerization inhibitor can be effectively utilized. Namely, this is suitable in both points of improvement in the product quality due to reduction in water in a product and prevention of precipitation (deposit) of a polymerization inhibitor.

It is preferable that an absorbing solvent 21 used in the above-mentioned absorbing column 20 contains one or more compounds selected from a N-oxyl compound, a phenol compound, a manganese salt, a dialkyldithiocarbamic acid copper salt, a nitroso compound and an amine compound and/or one or more or these compounds and phenothiazine. Even when one or more of these 6 compounds are combined with a phenothiazine compound to use as a 3 or more components system, the polymerization preventing effect equivalent to or superior over the effect of the 2-component system can be obtained.

It is preferable that the polymerization inhibitor used in the above absorbing column 20, the azeotropic distillation column 30 or the high boiling point substance separation column 40 contains one or more compounds selected from the group consisting of a N-oxyl compound, a phenol compound, a manganese salt such as manganese acetate, dialkyldithiocarbamic acid copper salt such as copper dibutyldithiocarbamate, a nitroso compound, and amine compound and phenothiazine. In addition, among a nitroso compound, there are substances which decompose and a component obtained by decomposition exerts the polymerization inhibition effect on acrylic acid, such as N-nitrosophenylhydroxyiamine or a salt thereof, for example, an ammonium salt of N-nitrosophenylhydroxylamine, p-nitrosophenol, N-nitrosodiphenylamine and ammonium salts thereof. The polymerization inhibitor in the process of FIG. 1 does not include such substances as a decomposition product of which has the polymerization inhibition effect.

The N-oxyl compound is not particularly limited, but any N-oxyl compounds which are generally known as a polymerization inhibitor for a vinyl compound can be used.

Among them, 2,2,6,6-tetramethylpiperidinooxyls represented by the following general formula (3) are suitably used.

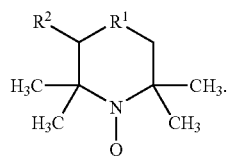

(3)

In the general formula (3), $R^1$ represents $CH_2$, CHOH, $CHCH_2OH$, $CHCH_2CH_2OH$, $CHOCH_2OH$, $CHOCH_2CH_2OH$, CHCOOH or C=O. $R^2$ represents a hydrogen atom or $CH_2OH$.

Examples of the above phenol compound include hydroquinone and methoquinone (p-methoxyphenol). Since the polymerization inhibiting effect when used combining with a N-oxyl compound and a phenothiazine compound is superior over that of hydroquinone, methoquinone is preferable. These phenol compounds can be used alone or in combination of two or more species.

Examples of the above phenothiazine compound include phenothiazine, bis-(α-methylbenzyl)phenothiazine, 3,7-dioctylphenothiazine, bis-(α-dimethylbenzyl)phenothiazine and the like.

The above-mentioned copper salt compound is not particularly limited, but any of an inorganic salt and an organic salt may be used. Examples thereof include copper dialkyldithiocarbamate, copper acetate, copper naphthenate, copper acrylate, copper sulfate, copper nitrate, copper chloride and the like. Any of monovalent and divalent these copper salt compounds may be used. Among the above-mentioned copper salt compounds, copper dialkyldithiocarbamate is preferable from a viewpoint of the effect etc.

Examples of the above manganese salt compound include manganase dialkyldithiocarbarnate, manganese diphenyldithiocarbamate, manganese formate, manganese acetate, manganese octanoate, manganese naphthenate, manganese permanganate, a manganese salt compound of ethylenediaminetetraacetic acid and the like having a same or different alkyl group selected from methyl, ethyl, propyl, and butyl. These may be used alone or in combination of two or more species.

An amount of the above-mentioned polymerization inhibitor is appropriately adjusted depending on the operation condition, being not particularly limited.

It is preferable that the polymerization inhibitor is dissolved in a solvent, and supplied as a polymerization inhibitor-containing solution. When supplied as a polymerization inhibitor-containing solution, since a polymerization inhibitor is uniformly dispersed in the column, this has advantage that the polymerization inhibiting effect becomes high. As a solvent for dissolving the polymerization inhibitor at absorbing column 20, an acrylic acid-containing solution is preferable. For example, when the acrylic acid is contained in the absorbing solvent 21, the absorbing solvent 21, or apart of acrylic acid obtained in other step, or a solution described later which is obtained after the acrylic acid oligomer is thermally decomposed, or a column bottom solution of an absorbing column can be used as an acrylic acid-containing solution. It is preferable that, in the absorbing column 20, in particular, a waste solution from steam ejector used in a step of producing acrylic acid is used as an acrylic acid-containing solution. A waste solution from a steam ejector is an aqueous solution containing acrylic acid, and since a composition ratio thereof is not considerably different from the solution composition in an absorbing column, thereby, reduction in the absorption efficiency in the absorbing column can be prevented. When the acrylic acid concentration in an acrylic acid-containing solution used is higher than an acrylic acid composition in an absorbing column, reduction in the absorption efficiency or polymerization may be caused.

Meanwhile, in case of the azeotropic distillation column 30, as a solvent for dissolving a polymerization inhibitor, an acrylic acid is preferable. Since water and a solvent are evaporated, but acrylic acid is not evaporated and is transferred to a column bottom side at a place above an aqueous acrylic acid solution supplying step of the distillation column 30 when supplied to, for example, the azeotropic distillation column 30, if acrylic acid is present, it is advantageous in that a polymerization inhibitor is accompanied with acrylic acid, and precipitation of a polymerization inhibitor can be prevented. When a thermal decomposition product of an acrylic acid oligomer is used as acrylic acid, acrylic acid is effectively utilized, and the productivity can be improved. In such the process, an oligomer refers to a Michael-type adduct of-acrylic acid represented by the following general formula (4);

R—COO—(X—COO)$_n$H    (4)

In the general formula (4), —X— denotes —$CH_2CH_2$— or —$CH(CH_3)$—, n denotes an integer of 1 to 5, provided that when n is 2 or more, plural —X-s may be the same or different.

In addition, as a polymerization Inhibitor having the thermal decomposition promoting activity used in the maleic acid separation column 46, the thin film evaporator 50 or the thermal decomposition vessel 51, among polymerization inhibitors which can be used in the above-mentioned absorbing column 20 one or more kinds of 4,4',4''-tris-(2,2,6,6-tetramethyl piperidinooxyl)phosphite and 2,2,6,6-tetramethylpiperidinooxyls represented by the following general formula (3).

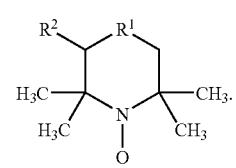

(3)

(In the above general formula (3), $R^1$ represents $CH_2$, CHOH, $CHCH_2OH$, $CHCH_2CH_2OH$, $CHOCH_2OH$, $CHOCH_2CH_2OH$, CHCOOH or C=O, and $R^2$ represents a hydrogen atom or $CH_2OH$), and one or more of N-hydroxy-2,2,6,6-tetramethylpiperidine compound such as 1,4-dihydroxy-2,2,6,6-tetramethylpiperidine, 1-hydroxy-2,2,6,6-tetramethylpiperidine and the like, and 2,2,6,6-tetramethylpiperidine compound such as 2,2,6,6-tetramethylpiperidine, 4-hydroxy-2,2,6,6-tetramethylpiperidine and the like can be used in combination.

Examples of an azeotropic solvent used in the azeotropic distillation column 30 include heptane, heptene, cycloheptane, cycloheptene, cycloheptadiene, cycloheptatriene, methylcyclohexane, ethylcyclopentane, dimethylcyclchexane, ethylcyclohexane, toluene, ethylbenzene, xylene, tetrachloroethylene, trichloropropene, dichlorobutane, chloropentane, chlorohexane, chlorobenzene and the like.

High purity acrylic acid can be obtained by distilling or crystallizing purified acrylic acid obtained from the high boiling point substance separation column 40 of FIG. 1. When distillation is performed, there can be used a method of adding, for example, the known primary amine such as hydrazine hydrate, phenylhydrazine and the like and/or a salt thereof together with purified acrylic acid to a distillation column at an amount of 1.0 to 10.0 mol, more preferably 1.0 to 5.0 mol relative to 1 mol of contained aldehyde, after adding the treating agent, performing distillation under reduced pressure and the like in a distillation column such as a flash column equipped with a mist separator under the conditions of a column top pressure of 10 to 150 hPa(abs.) and a column top temperature of 35 to 90° C. and the like. By this treatment, high purity acrylic acid having a content of aldehydes such as furfural, acrolein, benzaldehyde and the like of 10 weight ppm or smaller can be obtained. In addition, by crystallization using a crystallization device, equivalent high purity acrylic acid may be obtained. When a water-absorbing resin is produced from acrylic acid, since odor resulting from impurities contained in the acrylic acid or stimulation on a skin are not preferable in some utilities, it is preferable to use such the high purity acrylic acid.

The process for producing aliphatic carboxylic acid of the present invention has the constitution described hereinabove. Therefore, since operation conditions for a distillation column can be optimally set before a temperature and the separation condition which were previously a subject to be controlled are changed by detecting a change in supply amount of a solution to be distilled and the water concentration in advance, operation of a distillation column can be stabilized and, at the same time, a time during the non-steady state such as at starting up of operation of a distillation column can be shortened. In particular, when an apparatus is scaled up, since there is a tendency that a time lag to manifestation of influence on a distillation column becomes great, this effect of the present invention is remarkably exerted. In addition, when an easily polymerizable substance such as acrylic acid is handled, operation of a distillation column can be stabilized, and a time during the non-steady state at starting up of operation can be shortened. Therefore, since occurrence of a polymerization trouble can be reduced, there can be provided a process for producing aliphatic carboxylic acid which is industrially useful as a production raw material for forming various compounds and polymers.

BEST MODE FOR CARRYING OUT THE INVENTION

The present invention will be explained in detail below by way of Examples, but the present invention is not limited to these Examples. Unless indicated otherwise, "part" means "part by weight", and "%" means "% by weight".

EXAMPLE 1

Using an aqueous acrylic acid solution obtained by stripping acrolein from a solution obtained by absorbing acrylic acid in a reaction mixtures gas obtained by catalytic gas phase oxidation of propylene in water as a solution to be distilled, toluene as a azeotropic solvent, and a plate column of a total plate number of 50 having a perforated tray without downcomer as an azeotropic distillation column, azeotropic distillation was performed.

The aqueous acrylic acid solution contained 3% of acetic acid, 27% of water and 1.5% of others.

As the operation conditions for a distillation column, 5 T/hr of an aqueous acrylic acid solution was supplied to a 20th plate from the top plate, 10 T/hr of toluene was supplied to a top plate, and an amount of steam supplied by reboiler was controlled so as to give 60° C. of 15th plate from the top plate temperature. A column top pressure was controlled at 150 hPa, and an electric conductivity of an aqueous acrylic acid solution was continuously measured to detect the water concentration. As an amount of toluene to be supplied, an amount so that the water concentration in a column top vapor became 13% was set point-controlled by calculating, in a controlling apparatus, a target value of an amount of an azeotropic solvent to be supplied to an azeotropic distillation column from mass balance in a distillation column letting toluene and water not to be discharged from bottom liquid, setting the target value in a controlling apparatus, and performing automatical control of an amount of an azeotropic solvent to be supplied.

Then, the water concentration in an aqueous acrylic solution was gradually changed, and a change in a temperature distribution in a distillation column and a change in the concentration in bottom liquid were observed. Even when the water concentration in an aqueous acrylic acid solution was changed, both of a temperature distribution and a composition of bottom liquid were scarcely changed, and the systems was stably operated.

The azeotropic composition of toluene and water in the operation condition in Example 1 was found to contain approximately 15% of water.

COMPARATIVE EXAMPLE 1

According to the same manner as that of Example 1 except that an amount of steam to be placed into a reboiler was feedback-controlled by a column bottom temperature and an amount of toluene to be supplied was feedback-controlled at a 15th plate from top plate temperature in a method of controlling a distillation column, a distillation column was operated.

Both of a temperature at a distillation column and a composition of bottom liquid were varied due to a change in the water concentration in an aqueous acrylic acid solution, and 3 hours was required for returning to a steady value.

EXAMPLE 2

According to the same manner as that of Example 1 except that an amount of an aqueous acrylic acid solution to be supplied was changed, a distillation column was operated. Even when an amount of an aqueous acrylic acid solution to be supplied was changed, both of a temperature distribution and a composition of bottom liquid were scarcely changed, and the system could be stably operated.

COMPARATIVE EXAMPLE 2

According to the same manners as that of Example 2 except that an amount of steam to be placed into a reboiler was feedback-controlled by a column bottom temperature and an amount of toluene to be supplied was feedback-controlled by a 15th plate from top plate temperature in a method of controlling a distillation column, a distillation column was operated.

Both of a temperature at a distillation column and a composition of bottom liquid were varied due to a change in an amount of an aqueous acrylic acid solution to be supplied, and intervention of an operator was required in order to return to a steady value. 5 hours was required for return to a steady value.

EXAMPLE 3

Under the conditions of Example 1, operation of a distillation column was started by the following method.

Initially, an operation pressure of a distillation column was set at 150 hPa, crude acrylic acid after separation of water was charged into a column bottom, then the liquid was started to heat by supplying the steam into a reboiler. As soon as a temperature at a 15th plate from top plate in a column was started to be risen, supply of an aqueous acrylic acid solution was started and, at the same time, supply of toluene was started depending on an amount of water in a supply solution. An amount of steam corresponding to an amount of target supply was placed into a reboiler from the past operation record, and an amount of a solution to be supplied was adjusted to a target value of 10 T/hr in about 10 minutes. Thereafter, an amount of steam to be placed into a reboiler was finely adjusted so as to give 60° C. of a 15th plate from top plate temperature, and a distillation column was stabilized.

After stabilization of a distillation column, composition of bottom liquid was analyzed, and the water concentration was found to be 93 ppm, and the toluene concentration was found to be 18 ppm.

A required time from starting of supply of an aqueous acrylic acid solution to stabilization of a distillation column in the steady state was 30 minutes.

Operation was stopped 3 months after starting up, the interior of a column was inspected, and generation of a polymer was not seen in the interior.

The present application claims priority under 35 U.S.C. §119 to Japanese Patent Application No. 2003-134887, filed May 13, 2003, entitled "PROCESS FOR PRODUCING ALIPHATIC CARBOXYLIC ACID"

The content of that application is incorporated herein by reference in its entirety.

The invention claimed is:

1. A process for producing aliphatic carboxylic acid, which comprises an azeotropic distillation step of supplying an aqueous aliphatic carboxylic acid solution and an azeotropic solvent to an azeotropic distillation column to perform distillation, separating an azeotrope containing the azeotropic solvent and water as a distillate, and recovering aliphatic carboxylic acid with a reduced water content as bottom liquid, characterized in that a target value 2 of an amount of the azeotropic solvent to be supplied is set depending on an amount of water in the aqueous aliphatic carboxylic acid solution supplied to the azeotropic distillation column and wherein said target value 2 is determined by setting a target value 1 of the water concentration in a column top vapor, and by calculating mass balance of the azeotropic distillation column, and controlling the amount of the azeotropic solvent to be supplied at the target value 2.

2. The process for producing aliphatic carboxylic acid according to claim 1, wherein an amount of heat to be added to the azeotropic distillation column is adjusted so that the water concentration in bottom liquid of the azeotropic distillation column becomes not more than 500 ppm, and the azeotropic solvent concentration becomes not more than 500 ppm.

3. The process for producing aliphatic carboxylic acid according to claim 1, wherein a set value of the amount of heat to be added to the azeotropic distillation column is determined by a specified plate temperature in the azeotropic distillation column.

4. The process for producing aliphatic carboxylic acid according to claim 1, wherein the specified plate temperature is a temperature at a part corresponding to a 5th to 15th plate of theoretical plate which is counted from a column top.

5. The process for producing aliphatic carboxylic acid according to claim 1, wherein the aliphatic carboxylic acid is acrylic acid.

6. The process for producing aliphatic carboxylic acid according to claim 1, wherein the azeotropic solvent is at least one solvent selected from the group consisting of an aliphatic hydrocarbon having 7 to 8 carbon atoms, an aromatic hydrocarbon having 7 to 8 carbon atoms and a halogenated hydrocarbon having 2 to 6 carbon atoms.

7. The process for producing aliphatic carboxylic acid according to claim 1, wherein the target value 1 of the water concentration in a column top vapor at a range of 10% by weight of the azeotropic composition of an azeotropic solvent and water at a column top pressure is set.

8. A process for producing aliphatic carboxylic acid, which comprises an azeotropic distillation step of supplying an aqueous aliphatic carboxylic acid solution and an azeotropic solvent to an azeotropic distillation column to perform distillation, separating an azeotrope containing the azeotropic solvent and water as a distillate, and recovering aliphatic carboxylic acid with a reduced water content as bottom liquid, characterized in that a target value 2 of an amount of the azeotropic solvent to be supplied is set depending on an amount of water in the aqueous aliphatic carboxylic acid solution supplied to the azeotropic distillation column and a water concentration in a column top vapor, and the amount of the azeotropic solvent to be supplied is controlled at the target value 2, wherein a set value of the amount of heat to be added to the azeotropic distillation column is determined by a specified plate temperature in the azeotropic distillation column.

* * * * *